United States Patent

Fujimori

[11] 4,136,007
[45] Jan. 23, 1979

[54] SAMPLE APPLYING POSITION MARKING DEVICE FOR FILM FOR ELECTROPHORESIS

[75] Inventor: Ryo Fujimori, Hachiouji, Japan

[73] Assignee: Olympus Optical Co., Ltd., Tokyo, Japan

[21] Appl. No.: 906,681

[22] Filed: May 16, 1978

[30] Foreign Application Priority Data

May 21, 1977 [JP] Japan .................. 52/59185

[51] Int. Cl.² ..................... G01N 27/26; G01N 27/28
[52] U.S. Cl. ........................ 204/299 R; 204/180 G; 204/180 S; 424/12
[58] Field of Search ............ 204/180 G, 180 S, 299, 204/300; 23/230 B; 424/12

[56] References Cited

U.S. PATENT DOCUMENTS

| 3,421,998 | 1/1969 | Yallen | 204/180 S X |
|---|---|---|---|
| 3,428,547 | 2/1969 | Zec | 204/299 |
| 3,494,846 | 2/1970 | Arquembourg | 204/180 G |
| 3,499,360 | 3/1970 | Davis | 204/180 G X |
| 3,616,387 | 10/1971 | Siebert et al. | 204/180 G |
| 3,622,484 | 11/1971 | Cawley | 204/180 G |
| 3,755,121 | 8/1973 | Schlutz | 204/180 G |
| 3,762,877 | 10/1973 | Rains et al. | 204/180 G X |
| 3,773,646 | 11/1973 | Mandle et al. | 204/299 |
| 3,801,491 | 4/1974 | Cawley | 204/299 |
| 3,930,973 | 1/1976 | Nerenberg et al. | 204/180 S |

*Primary Examiner*—Arthur C. Prescott
*Attorney, Agent, or Firm*—Cushman, Darby & Cushman

[57] ABSTRACT

A sample applying position marking device for film for electrophoresis comprising a base having a frame which serves as reference surfaces, a top plate mounted to the base so that the top plate can be swung in respect to the base, and pointed protuberances mounted at pre-determined intervals on the bottom surface of the top plate. The sample applying position marking device is arranged to form marks at pre-determined positions of a film by means of the pointed protuberances mounted to the top plate when the film is placed on the base by matching the film to the frame and the top plate is swung downward.

7 Claims, 5 Drawing Figures

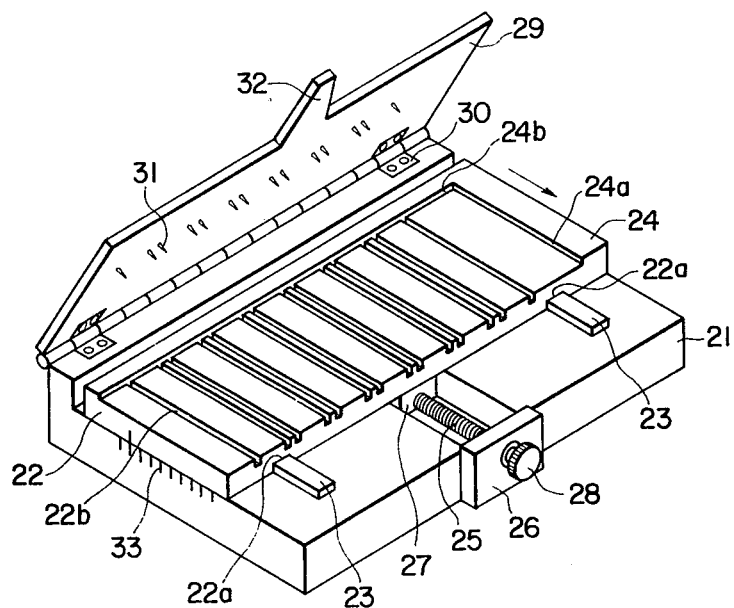

SAMPLE APPLYING POSITION MARKING DEVICE FOR FILM FOR ELECTROPHORESIS

BACKGROUND OF THE INVENTION (a) Field of the Invention

The present invention relates to a sample applying position marking device for film for electrophoresis and, more particularly, to a sample applying position marking device to be used for marking the positions for applying the liquid samples such as blood serums onto the film for the purpose of electrophoresis.

(b) Description of the Prior Art

To analyze liquid samples such as blood serums by electrophoresis, the samples are applied onto a film such as a filter paper, cellulose acetate film or the like (hereinafter referred to as film) in straight lines and are energized through the film so that fractionated patterns of samples are formed. The film on which the fractionated patterns are formed is subjected to such processes as dyeing, decolorization, etc. and, then, subjected to colorimetric analysis by a densitometer. In the above-mentioned electrophoresis, one of known methods for applying the blood serum samples onto the film is to suck the blood serum into a micropipette and to draw a line on the film by using the micropipette. Recently, however, densitometers have been improved and automatized so that the fractionated patterns on the film are automatically analyzed in turn and recorded when the film, on which the fractionated patterns to be measured are formed, is just fed into the densitometer. When performing colorimetric analysis by such densitometer, it is necessary to apply the blood serum smaples so that the distance from the leading end of the film to the blood serum samples applied at the first position and the pitch between blood serum samples applied at respective positions become the pre-determined values which are suitable for the construction of the densitometer to be used. For this purpose, as shown in FIG. 1, marks 3 are formed on the film 1 beforehand at the positions of both ends of respective blood serum samples 2 so that the distance from the leading end of the film to the blood serum sample to be applied at the first position becomes a, the pitch between respective blood serum samples becomes p (a and p are measured by using the centers of respective blood serum samples to be applied as the standard points), and the distance from the side edge of the film to the blood serum samples in the width direction of the film becomes d. Then, the blood serum samples are applied in proper positions by utilizing those marks 3. In the known method, those marks 3 are formed by manual work. That is, a scale 4 is placed on the film 1 as shown in FIG. 2 and pinholes to be used as marks 3 are formed into the film by a needle or the like or marks 3 are formed by a pencil by reading the graduations of the scale 4. Therefore, the marking work is very inefficient.

SUMMARY OF THE INVENTION

It is, therefore, a primary object of the present invention to provide a sample applying position marking device for film for electrophoresis comprising a base having reference surfaces, a top plate engageably mounted to the base, and plurality of needles provided to the top plate, the sample applying position marking device being arranged to form marks for positions for applying the samples at the pre-determined positions of a film to be used for electrophoresis by placing the film onto the base matching the film to the reference surfaces and by engaging the top plate with the pre-determined position of the base.

Another object of the present invention is to provide a sample applying position marking device for film for electrophoresis arranged to vary the positions of reference surfaces provided to the base so that the positions of marks to be formed on the film can be varied.

Still another object of the present invention is to provide a sample applying position marking device for film for electrophoresis further comprising a cutting blade mounted to a side face of the base and another cutting blade mounted to a side face of the top plate which corresponds to the above-mentioned side face of the base, the sample applying position marking device being arranged to cut off the film at the same time as the top plate is engaged with the base for the purpose of marking the sample applying positions on the film.

BRIEF DESCRIPTION OF THE DRAWINGS

FIG. 4 shows a perspective view of a second embodiment of the present invention; and FIG. 5 shows a perspective view of a third embodiment of the present invention.

DETAILED DESCRIPTION OF THE PREFERRED EMBODIMENTS

Figure 1:
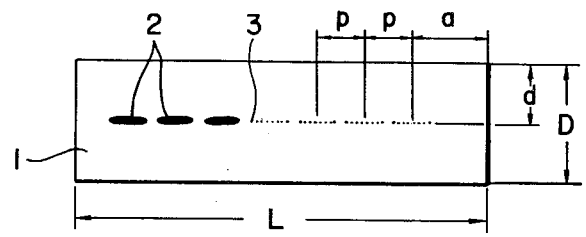
FIG. 1 shows a plan view illustrating the sample applying positions on the film.
Figure 2:
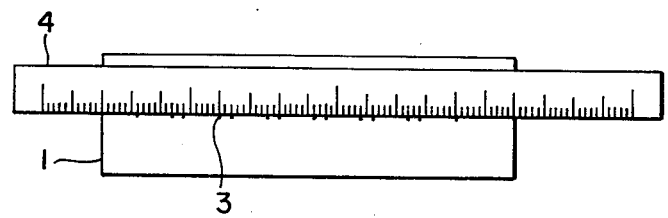
FIG. 2 shows a plan view illustrating a known method for forming the marks on the film.
Figure 3:
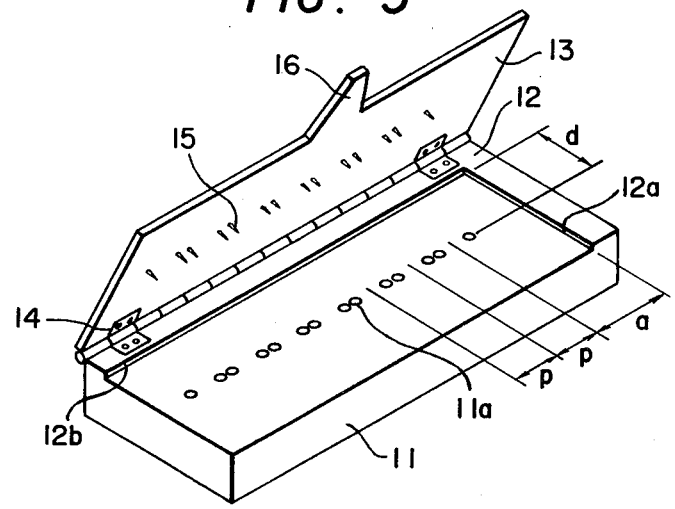
FIG. 3 shows a perspective view of a first embodiment of the present invention.

In the following, the concrete construction of the sample applying position marking device for film for electrophoresis according to the present invention is described referring to respective embodiments shown on the accompanying drawings. A first embodiment of the device according to the present invention is shown in FIG. 3. In FIG. 3, numeral 11 designates a base on which a frame 12 having reference surfaces 12a and 12b is fixed or formed integral with the base. Numeral 13 designates a top plate which is mounted to the base 11 through hinges 14 so that the top plate 13 can be engaged with and disengaged from the base 11. Numeral 15 designates a plural number of needles mounted to the top plate 13. In the base 11, holes 11a are formed at those positions corresponding to the needles 15 so that the needles 15 enter the holes 11a when the top plate 13 is engaged with the base 11. The positions of the holes 11a are decided so that they correspond with the positions of marks 3 shown in FIG. 1. That is, the positions of the holes 11a are decided so that the distance from the reference surface 12a to the center between the holes at both ends of the first blood serum sample applying position becomes equal to a, the pitch between respective blood serum samples becomes equal to p, and the distance from the reference surface 12b to respective holes becomes equal to d. Numeral 16 designates a lever provided to the top plate 13.

To mark the sample applying positions by the above-mentioned device, the film is placed on the base 11 by matching its edges to the reference surfaces 12a and 12b and, then, the top plate 13 is engaged with the base 11 by pushing down the lever 16. When the length of the needles 15 is decided so that the ends of the needles 15 come to a height lower than the top surface of the base 11 when the top plate 13 is engaged with the base 11, respective needles 15 enter the corresponding holes 11a at that time and pinholes are formed in the film by means of the needles 15. Those pinholes are formed at the positions of marks 3 in FIG. 1. When springs are provided in combination with the hinges 14 in order to keep the top plate 13 normally disengaged from the base 11, it is more convenient for using the device.

Now, FIG. 4 shows a second embodiment of the device according to the present invention. Out of the dimensions related to the sample applying positions, the distance d shown in FIG. 1 differs with the kind of the film to be used. Therefore, to obtain proper fractionated patterns, it is essential to adjust the distance d from one side edge of the film to the marking position to a predetermined value which is suitable for the kind of the film to be used. The second embodiment shown in FIG. 4 is arranged to vary the value d, i.e., the distance of marking position from the side edge of the film. In FIG. 4, numeral 21 designates a base, numeral 22 designates a slide mounted on the base 21 and arranged to be slidable in the direction shown by the arrowhead by means of guide grooves 22a formed at the bottom of the slide 22 and guides 23 mounted on the base 21. At the top of the slide 22, a plurality of long slots 22b are formed in the moving direction of the slide 22. Numeral 24 designates a frame formed on the slide 22 and having reference surfaces 24a and 24b. Numeral 25 designates a feed screw supported by a supporting plate 26 which is mounted to the base 21. Numeral 27 designates a nut fixed at the bottom of the slide 22 and screwed onto the feed screw 27. Numeral 28 designates a knob to be rotated in order to rotate the feed screw 27 and to thereby move the slide 22. Numeral 29 designates a top plate which is mounted to the base 21 through hinges 30 so that the top plate 29 can be engaged with and disengaged from the base 21. Numeral 31 designates needles mounted to the bottom surface of the top plate 29. Numeral 32 designates a lever and numeral 33 designates graduations.

To mark the sample applying positions by the device of the above-mentioned second embodiment, the film is placed on the top surface of the slide 22 by matching its edges to the reference surfaces 24a and 24b and, then, the top plate 29 is engaged with the slide 22 by pushing down the lever 32. Thus, pinholes are formed in the film. In case of this embodiment, it is possible to vary the position for forming the pinholes, i.e., the distance from the reference surface 24b to the pinholes, by moving the slide 22 in respect to the base 21. In other words, it is possible to vary the value d shown in FIG. 1. Therefore, when the device of the second embodiment is used, it is possible to form the marks at the desired position even when the kind of the film becomes different. Though this embodiment is arranged to vary the value d by moving the slide 22 on which the film is to be placed, it is also possible to arrange so that the frame having reference surfaces (the frame 12 in FIG. 3 or frame 24 in FIG. 4) is moved for the purpose of varying the value d. In that case, the plate on which the film is to be placed (the base 11 in FIG. 3 or slide 22 in FIG. 4) may have holes as shown in FIG. 3 instead of long slots.

Now, FIG. 5 shows a third embodiment of the device according to the present invention which is arranged to form the marks and, at the same time, to cut the film to a pre-determined length when the film to be used is wound in the form of roll. In FIG. 5, numeral 41 designates a base, numeral 42 designates a top plate, and numerals 43 and 44 respectively designate cutter blades.

The cutter blade 43 is mounted to the side face of the top plate 42 and the cutter blade 44 is mounted to the side face of the base 41. The other parts are constructed substantially same as the first and second embodiments. Therefore, their detailed explanation is omitted here. To mark the sample applying positions by the device of the above-mentioned third embodiment, the film unwound from the film roll 40 is placed on the base 41 by matching its leading edge and side edge to the reference surfaces of the frame 45, which is provided to the base 41, and then the top plate 42 is engaged with the base 41 by pushing it down. Thus, the marks are formed in the film in the same way as the cases of the first and second embodiments and, at the same time, the film is cut off by the cutter. When the distance L from the reference surface of the frame 45 to the cutter is made equal to the required length of the film, the film is always cut to that length.

In the above-mentioned embodiments, it is arranged to form pinholes by using needles. However, the marking method is not limited to the above. For example, it is also possible to use pointed protuberances instead of needles and to thereby mark small dots with ink or the like or to form small indentations in order to use them as marks. Besides, the position for mounting the needles is not limited to the top plate. It is also possible to mount the needles in the holes or slots formed in the base or the like and to arrange that the needles are moved upward through a lever or other suitable means, when the top plate is pushed down, so that the marks are formed in the film.

As explained in the above, by the marking device according to the present invention, it is possible to form the marks at the pre-determined correct positions by simple operation to push down the top plate only. Besides, in case of the third embodiment, it is possible to cut the film to the pre-determined length at the same time as the marks are formed in the film. Therefore, it is very effective especially when using the film which is wound in the form of roll.

I claim:

1. A sample applying position marking device for film for electrophoresis comprising a base having reference surfaces, a top plate arranged to move upward and downward on said base and to contact the top surface of said base when said top plate is moved downward, and pointed protuberances mounted to pre-determined positions on the surface of said top plate which contacts the top surface of said base when said top plate is moved downward, said sample applying position marking device for film for electrophoresis being arranged to form marks onto a film by placing the film on said base matching the film to said reference surfaces and by moving said top plate downward.

2. A sample applying position marking device for film for electrophoresis according to claim 1, in which said top plate is hinged to said base plate so that said top plate can be freely swung upward and downward in respect to said base.

3. A sample applying position marking device for film for electrophoresis according to claim 1, in which said pointed protuberances are mounted at pre-determined positions on the top surface of said base.

4. A sample applying position marking device for film for electrophoresis according to claim 1, in which said reference surfaces of said base are arranged to be movable.

5. A sample applying position marking device for film for electrophoresis comprising a base, a slide having reference surfaces and slidably mounted to said base, a top plate arranged to move upward and downward on said slide and to contact the top surface of said slide when said top plate is moved downward, and pointed protuberances mounted to pre-determined positions on the surface of said top plate which contacts the top surface of said slide when said top plate is moved downward, said sample applying position marking device for film for electrophoresis being arranged to form marks onto a film by placing the film on said slide matching the film to said reference surfaces and by moving said top plate downward.

6. A sample applying position marking device for film for electrophoresis according to claim 5, in which said pointed protuberances are mounted at pre-determined positions on the top surface of said slide.

7. A sample applying position marking device for film for electrophoresis according to claim 1 further comprising a lower cutting blade mounted to a side face of said base and an upper cutting blade mounted to a side face of said top plate corresponding to said side face of said base, said sample applying position marking device for film for electrophoresis being arranged to form marks onto a film and, at the same time, to cut off the film by said upper cutting blade and said lower cutting blade when the film is placed on said base by matching the film to said reference surfaces and said top plate is moved downward.

* * * * *